US00PP08063P

United States Patent [19]

Meilland

[11] Patent Number: Plant 8,063

[45] Date of Patent: Dec. 22, 1992

[54] ROSE PLANT — MEIGHIVON VARIETY

[75] Inventor: Alain A. Meilland, Antibes, France

[73] Assignee: The Conard-Pyle Company, West Grove, Pa.

[21] Appl. No.: 710,554

[22] Filed: Jun. 5, 1991

[51] Int. Cl.[5] ..... A01H 5/00

[52] U.S. Cl. ..... Plt./8.1

[58] Field of Search ..... Plt. 7, 8, 8.1, 8.2

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which forms abundantly and continuously attractive long lasting very double blossoms. The new variety is a spontaneous mutation of the Meilarco variety (U.S. Plant Pat. No. 6,170). The blossoms of the new variety while similar in shape to those of the Meilarco variety possess a distinctive white coloration which sometimes turns yellowish toward the center when fully open instead of the pastel romantic pink coloration of the parent variety. The plant is bushy, forms dark green glossy foliage, and forms very vigorous vegetation. Additionally, the plant is not particularly affected by cryptogamic diseases.

1 Drawing Sheet

SUMMARY OF THE INVENTION

The new variety of Miniature rose plant is a spontaneous mutation of unknown causation of the MEILARCO variety (U.S. Plant Pat. No. 6,170). Such new variety was discovered during the selective study of the plants of the MEILARCO variety created by grafting.

It was found that the growth habit and foliage of the new variety is substantially the same as that of its parent. Also, the flower configuration is very similar. However, the new variety has been found to exhibit a distinctive blossom coloration which is white and commonly turns yellowish toward the center when fully open instead of the pastel romantic pink coloration of the parent variety.

In view of its distinctive blossom appearance the new variety has been carefully preserved and studied. Had it not been for my efforts it would have been lost to mankind.

It was found that the new variety of Miniature rose plant of the present invention possesses the following combination of characteristics:

(a) forms in abundance on a continuous basis attractive very double long lasting blossoms which are white and commonly turn yellowish toward the center when fully open,
(b) forms very vigorous vegetation with dark green and glossy foliage,
(c) exhibits a bushy growth habit,
(d) forms light green adult wood, and
(e) is not particularly affected by cryptogamic diseases.

The new variety well meets the needs of the horticultural industry. It is particularly well-suited for use as attractive ornamentation when grown in parks and gardens.

The new variety has been found to undergo asexual propagation by a number of routes, including budding, grafting, cuttage, etc.

Asexual propagation by the above mentioned methods as performed in France has shown conclusively that the characteristics of the new variety are strictly transmissible from one generation to another.

The new variety has been named the Meighivon variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during October while growing on their own roots in greenhouses at Le Cannet des Maures, Var, France.

DETAILED DESCRIPTION

Figures 1, 2, 3, 4, 5, 6, 7, 8, 9, 10, 11, 12, 13, 14, 15, 16:
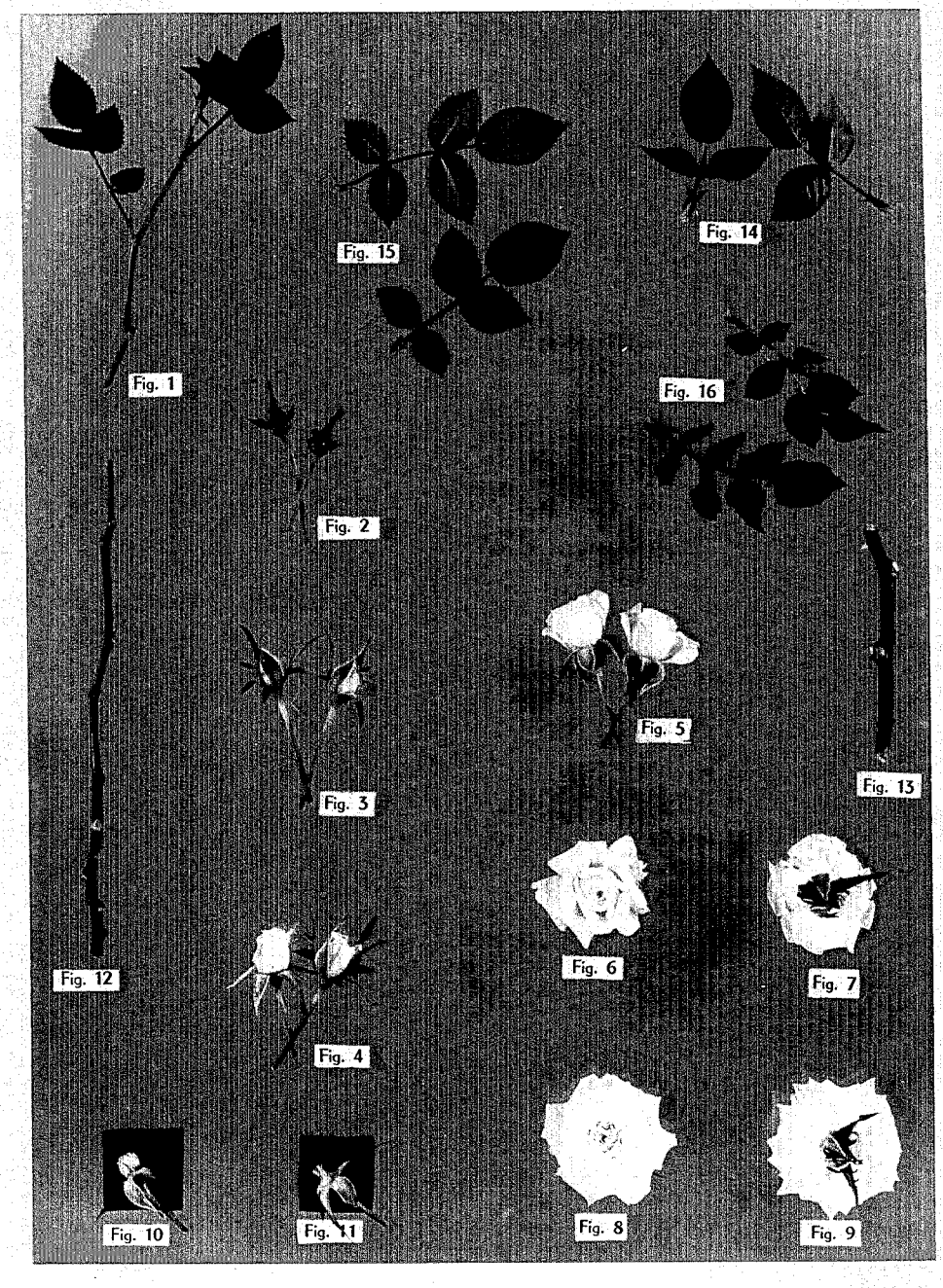
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates specimens of two flowers in the course of opening.
FIG. 6 illustrates a specimen of a flower in the course of opening — plan — obverse.
FIG. 7 illustrates a specimen of a flower in the course of opening — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown on the left and the under surface being shown on the right.
FIG. 15 illustrates specimens of leaves with five leaflets with the under surface being shown on the top and the upper surface being shown on the bottom.
FIG. 16 illustrates specimens of leaves with seven leaflets with the under surface being shown at the top right and the upper surface being shown at the lower left.

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety which were observed during October while growing on their own roots in greenhouses at Le Cannet des Maures, Var, France.

Class: Miniature.

Plant:

*Height.*—Approximately 30 cm. on average.

*Habit.*—Bushy.

Branches:

*Color.*—Young stems: lettuce green, Yellow-Green Group 144A, sometimes slightly stained with reddish coloration. Adult wood: light green, Yellow-Green Group 146B.

*Thorns.*—Size: medium to large. Quantity: average. Color: pinkish on young stems and pinkish-greenish changing to tan on adult wood.

Leaves:

*Petioles.*—Upper surface: striped, reddish brown on young foliage and light green on adult foliage with glandular edges. Under surface: light green with a few crooked prickles.

*Stipules.*—Adnate, pectinate, somewhat wide and linear, striped reddish brown on young leaves, and light green on adult wood with glandular edges.

*Leaflets.*—Number: rarely 3, 5 (most often), and somtimes 7. Shape: elliptic. Serration: single and regular. Texture: leathery. General appearance: dark green foliage, bright and dense. Color (young foliage): Upper surface: lettuce green, Yellow-Green Group 144A, edged with reddish coloration and more or less suffused with reddish brown coloration. Under surface: lettuce green, Yellow-Green Group 144A, and edged with reddish coloration. Color (adult foliage): Upper surface: dark bright green, Yellow-Green Group 147A. Under surface: medium green, Yellow-Green Group 147B.

Inflorescence:

*Number of flowers.*—Approximately 1 to 5 per stem.

*Peduncle.*—Medium green, straight, rigid and smooth, its length is approximately 6 cm. on average.

*Sepals.*—Upper surface: tomentose and greenish in coloration. Under surface: smooth, medium green, and the outer sepals have very appendiculated edges.

*Buds.*—Shape: ovoid. Length: approximately 2 cm. on average. Size: fairly large. Color upon opening: Upper surface: white, White Group 155B, turning light yellow, Yellow Group 4C, at the base. Under surface: white, White Group 155A, and the outer petals are sometimes tinted with Yellow-Green Group 145A towards the edge and bottom of the petals.

Flower.—form: very double, very slightly globular changing to cuplike. Diameter: approximately 6 to 7 cm. on average. Color (when opening begins): Upper surface: white, White Group 155B. under surface: white, White Group 155A. Color (when blooming): Upper surface: white, White Group 155B. Under surface: white White Group 155A. Color (at end of blooming): Upper surface: white, White Group 155B, turning yellowish when fully open. Under surface: white, White Group 155A. Fragrance: slight. Lasting quality: long. Petal number: approximately 85 to 95 on average. Petal texture: consistent and fairly thick. Petal drop: fair. Anthers: very often a vegetative center is formed on young plants which commonly includes a few light yellow stamens, and on older plants there commonly are only very few stamens and pistils which are light yellow in coloration. Receptacle: light green, and in longitudinal section it is narrow and in the shape of a pitcher.

Development:

*Vegetation.*—Vigorous.

*Blooming.*—Very abundant.

*Aptitude to bear fruit.*—Poor.

*Resistance to frost.*—Good.

*Resistance to diseases.*—Good.

I claim:

1. A new and distinct variety of Miniature rose plant characterized by the following combination of characteristics:

(a) forms in abundance on a continuous basis attractive very double long lasting blossoms which are white and commonly turn yellowish toward the center when fully open, (b) forms very vigorous vegetation with dark green and glossy foliage, (c) exhibits a bushy growth habit, (d) forms light green adult wood, and (e) is not particularly affected by cryptogamic diseases;

substantially as herein shown and described.

* * * * *